United States Patent
Weber

(10) Patent No.: US 8,862,203 B2
(45) Date of Patent: Oct. 14, 2014

(54) MEDICAL DEVICE WITH TEMPERATURE MODULATOR FOR USE IN MAGNETIC RESONANCE IMAGING

(75) Inventor: Jan Weber, Maple Grove, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 2599 days.

(21) Appl. No.: 10/401,227

(22) Filed: Mar. 27, 2003

(65) Prior Publication Data

US 2004/0193039 A1    Sep. 30, 2004

(51) Int. Cl.
| | | |
|---|---|---|
| *A61B 5/00* | (2006.01) | |
| *A61B 5/055* | (2006.01) | |
| *A61M 25/01* | (2006.01) | |
| *G01R 33/56* | (2006.01) | |
| *G01R 33/28* | (2006.01) | |
| *A61M 25/00* | (2006.01) | |
| *A61B 19/00* | (2006.01) | |

(52) U.S. Cl.
CPC ............ *A61B 19/54* (2013.01); *A61M 25/0045* (2013.01); *A61B 5/055* (2013.01); *A61B 2019/5454* (2013.01); *A61M 25/0127* (2013.01); *G01R 33/5601* (2013.01); *G01R 33/281* (2013.01); *A61M 25/0009* (2013.01); *G01R 33/285* (2013.01)
USPC ............ 600/420; 604/531; 324/309; 324/315

(58) Field of Classification Search
USPC ................. 600/415, 410; 604/530–532, 95.5, 604/95.05; 607/103
See application file for complete search history.

(56) References Cited

U.S. PATENT DOCUMENTS

| | | |
|---|---|---|
| 2,863,174 A | 12/1958 | Schuman et al. |
| 3,620,876 A | 11/1971 | Guglielmo, Sr. et al. |
| 3,874,207 A | 4/1975 | Lemelson |
| 3,957,943 A | 5/1976 | Ogura |
| 3,993,529 A | 11/1976 | Farkas |
| 4,003,554 A | 1/1977 | Chauffoureaux |
| 4,035,547 A | 7/1977 | Heller, Jr. et al. |
| 4,035,598 A | 7/1977 | Van Amsterdam |
| 4,040,162 A | 8/1977 | Isogai et al. |
| 4,093,484 A | 6/1978 | Harrison |

(Continued)

FOREIGN PATENT DOCUMENTS

| | | |
|---|---|---|
| DE | 199 54 960 A1 | 6/2000 |
| EP | 0 101 595 A1 | 2/1984 |

(Continued)

OTHER PUBLICATIONS

Gleich, Bernhard, "Catheter Temperature Mesurement with Ferromagnets," Research Disclosure, Kenneth Mason Publications, vol. 442, No. 15, (Feb. 2001).

(Continued)

*Primary Examiner* — Unsu Jung
*Assistant Examiner* — Amanda Lauritzen Moher
(74) *Attorney, Agent, or Firm* — Seager, Tufte & Wickhem LLC

(57) ABSTRACT

This disclosure employs temperature, magnetism and Curie point transition to construct and use catheters and other medical devices that can be visualized using magnetic resonance imaging (MRI). Accordingly, this disclosure includes, but is not limited to, medical devices, means of constructing medical devices, and methods of imaging medical devices using magnetic resonance and other technologies.

19 Claims, 8 Drawing Sheets

(56) References Cited

U.S. PATENT DOCUMENTS

| | | | |
|---|---|---|---|
| 4,143,112 A | 3/1979 | Turner | |
| 4,298,324 A | 11/1981 | Soulier | |
| 4,339,295 A | 7/1982 | Boretos et al. | |
| 4,390,482 A | 6/1983 | Feurer | |
| 4,407,651 A | 10/1983 | Beck et al. | |
| 4,454,234 A | 6/1984 | Czerlinski | |
| 4,483,341 A | 11/1984 | Witteles | |
| 4,568,262 A | 2/1986 | Feurer | |
| 4,671,757 A | 6/1987 | Volk, Jr. | |
| 4,672,972 A | 6/1987 | Berke | |
| 4,760,228 A | 7/1988 | Kudo | |
| 4,764,394 A | 8/1988 | Conrad | |
| 4,859,380 A | 8/1989 | Ogata | |
| 4,860,744 A | 8/1989 | Johnson et al. | |
| 4,930,494 A | 6/1990 | Takehana et al. | |
| 4,950,239 A | 8/1990 | Gahara et al. | |
| 4,977,886 A | 12/1990 | Takehana et al. | |
| 4,989,608 A | 2/1991 | Ratner | |
| 5,104,593 A | 4/1992 | Joseph | |
| 5,154,179 A | 10/1992 | Ratner | |
| 5,172,551 A | 12/1992 | Nakajima et al. | |
| 5,207,227 A | 5/1993 | Powers | |
| 5,222,543 A | 6/1993 | Carlstrom et al. | |
| 5,290,266 A | 3/1994 | Rohling et al. | |
| 5,296,272 A | 3/1994 | Matossian et al. | |
| 5,324,345 A | 6/1994 | Rutjes et al. | |
| 5,330,742 A | 7/1994 | Deutsch et al. | |
| 5,352,871 A | 10/1994 | Ross et al. | |
| 5,411,730 A | 5/1995 | Kirpotin et al. | |
| 5,421,832 A | 6/1995 | Lefebvre | |
| 5,429,583 A | 7/1995 | Paulus et al. | |
| 5,433,717 A | 7/1995 | Rubinsky et al. | |
| 5,496,311 A | 3/1996 | Abele et al. | |
| 5,514,379 A | 5/1996 | Weissleder et al. | |
| 5,622,665 A | 4/1997 | Wang | |
| 5,628,950 A | 5/1997 | Schrenk et al. | |
| 5,641,423 A | 6/1997 | Bridges et al. | |
| 5,653,778 A | 8/1997 | Rutjes et al. | |
| 5,690,109 A | 11/1997 | Govind et al. | |
| 5,693,376 A | 12/1997 | Fetherston et al. | |
| 5,706,810 A | 1/1998 | Rubinsky et al. | |
| 5,720,939 A | 2/1998 | Schröder | |
| 5,728,079 A | 3/1998 | Weber et al. | |
| 5,744,958 A | 4/1998 | Werne | |
| 5,762,741 A | 6/1998 | Kodokian | |
| 5,762,972 A | 6/1998 | Byon | |
| 5,773,042 A | 6/1998 | Amano et al. | |
| 5,775,338 A | 7/1998 | Hastings | |
| 5,787,959 A | 8/1998 | Laxmanan et al. | |
| 5,817,017 A | 10/1998 | Young et al. | |
| 5,844,217 A | 12/1998 | Hawley et al. | |
| 5,855,553 A | 1/1999 | Tajima et al. | |
| 5,908,410 A * | 6/1999 | Weber et al. | 604/523 |
| 5,948,194 A | 9/1999 | Hill et al. | |
| 5,951,513 A | 9/1999 | Miraki | |
| 6,004,289 A | 12/1999 | Saab | |
| 6,035,657 A | 3/2000 | Dobak, III et al. | |
| 6,040,019 A | 3/2000 | Ishida et al. | |
| 6,056,844 A | 5/2000 | Guiles | |
| 6,061,587 A | 5/2000 | Kucharczyk et al. | |
| 6,123,920 A | 9/2000 | Gunther et al. | |
| 6,137,093 A | 10/2000 | Johnson, Jr. | |
| 6,176,857 B1 | 1/2001 | Ashley | |
| 6,190,355 B1 | 2/2001 | Hastings | |
| 6,203,777 B1 | 3/2001 | Schröder | |
| 6,207,134 B1 | 3/2001 | Fahlvik et al. | |
| 6,224,536 B1 | 5/2001 | Pike | |
| 6,231,516 B1 | 5/2001 | Keilman et al. | |
| 6,248,196 B1 | 6/2001 | Waitz et al. | |
| 6,270,707 B1 | 8/2001 | Hori et al. | |
| 6,270,711 B1 | 8/2001 | Gellert et al. | |
| 6,272,370 B1 * | 8/2001 | Gillies et al. | 600/411 |
| 6,280,384 B1 | 8/2001 | Loeffler | |
| 6,352,779 B1 | 3/2002 | Edwards et al. | |
| 6,361,759 B1 | 3/2002 | Frayne et al. | |
| 6,368,994 B1 | 4/2002 | Sklyarevich | |
| 6,418,337 B1 | 7/2002 | Torchia et al. | |
| 6,478,911 B1 | 11/2002 | Wang et al. | |
| 6,522,926 B1 | 2/2003 | Kieval et al. | |
| 6,622,731 B2 * | 9/2003 | Daniel et al. | 128/898 |
| 6,696,121 B2 | 2/2004 | Jung, Jr. et al. | |
| 6,788,060 B1 * | 9/2004 | Feenan et al. | 324/320 |
| 6,850,804 B2 * | 2/2005 | Eggers et al. | 607/103 |
| 7,048,716 B1 * | 5/2006 | Kucharczyk et al. | 604/164.01 |
| 7,389,778 B2 * | 6/2008 | Sabo et al. | 128/899 |
| 2001/0043998 A1 | 11/2001 | Chen et al. | |
| 2001/0054775 A1 | 12/2001 | Nandu et al. | |
| 2002/0095198 A1 | 7/2002 | Whitebook et al. | |
| 2003/0055449 A1 | 3/2003 | Lee et al. | |
| 2004/0019447 A1 * | 1/2004 | Shachar | 702/115 |
| 2004/0136905 A1 * | 7/2004 | Kent et al. | 424/1.11 |
| 2005/0043611 A1 * | 2/2005 | Sabo et al. | 600/411 |
| 2006/0036301 A1 * | 2/2006 | Eggers et al. | 607/103 |
| 2011/0135356 A1 * | 6/2011 | Baba et al. | 399/329 |

FOREIGN PATENT DOCUMENTS

| | | |
|---|---|---|
| EP | 0 355 423 A2 | 2/1990 |
| EP | 0 525 069 B1 | 3/1996 |
| JP | 2001314390 | 11/2001 |
| WO | WO 80/02124 | 10/1980 |
| WO | WO 89/11874 A1 | 12/1989 |
| WO | WO 98/52064 A1 | 11/1998 |
| WO | WO 99/03306 | 1/1999 |
| WO | WO 00/64608 | 11/2000 |
| WO | WO 01/51115 | 1/2001 |
| WO | WO 03/035161 A1 | 5/2003 |

OTHER PUBLICATIONS

Glowinski et al., "Catheter Visualization Using Locally Induced Actively Controlled Field Inhomogeneities" Magnetic Resonance in Medicine, vol. 38, No. 2, pp. 253-258 (Aug. 1997).

Hofman et al., "Transesophageal Cardiac Pacing During Magnetic Resonance Imaging: Feasibility and Safety Considerations," Magnetic Resonance in Medicine, vol. 35, No. 3 (Mar. 1996).

International Search Report for PCT/US2004/002554, issued Aug. 20, 2004.

Ashley, S., assoc. ed., "Electric Plastics," *Mechanical Engineering*, Apr. 1998, http://www.memagazine.org/backissues/apri98/features/plastics/plastics.html (Jul. 3, 2003).

Ballinger, J.R., "MRI Contrast Agents," *MRI Tutor Web Site*, http://www.mritutor.org/mritutor/contrast.html (Aug. 8, 2002).

Ballinger, J.R. "Introduction to MRI," *MRI Tutor Web Site*, http://www.mritutor.org/mritutor/index.html (Jul. 3, 2003).

Bowman, M., "The Big Chill," http://www.ameslab.gov/News/Inquiry/fall97/bigchill.html (Aug. 8, 2002).

Exploratorium, "Curie Point," http://www.exploratorium.edu/snacks/curie_point.html (Jul. 3, 2003).

Exploratorium, "Curie Temperature," Abstract from http://www.exploratorium.edu/serf/phenomena/curie_temperature.html (Aug. 8, 2002).

Gavrin, "What Is Physics Good for?", IUPUI, http://webphysics.iupui.edu/251/251Sp97GFApr28.html (Aug. 8, 2002).

Gould, T.A., "How MRI Works," http://www.howstuffworks.com/mri.htm (Aug. 8, 2002).

Gould, T.A., "How MRI Works," http://electronics.howstuffworks.com/mri.htm/printable (Jul. 3, 2003).

Hesselink, J.R. "Basic Principles of MR Imaging," http://spinwarp.ucsd.edu/NeuroWeb/Test/br-100.htm (Jul. 3, 2003).

Hornak, J.P., *The Basics of MRI*, http://www.cis.rit.edu/htbooks/mri/chap-1/chap-1.htm, Chapters 1 and 3 (Jan. 4, 2002).

Hornak, J.P., *The Basics of MRI*, http://www.cis.rit.edu/htbooks/mri, Chapters 1, 2, 6, 8 and 9 (Jul. 3, 2003).

King, M.M., "Module #2: Basic Principles of MRI," http://www.erads.com/mrimod.htm (Aug. 8, 2002).

Koehler, K.R., "Body Temperature Regulation," http://www.rwc.uc.edu/Koehler/biophys/8d.html (Jul. 8, 2003).

Konings, at al., "Heating Around Intravascular Guidewires by Resonating RF Waves," Abstract from *J. Magn. Reson. Imaging*, 12(1):79-85 (2000).

(56) References Cited

OTHER PUBLICATIONS

Kuperman, V., *Magnetic Resonance Imaging: Physical Principles and Applications*, Academic Press (2000).

"Laboratory #27: Peltier Elements and Thermistors," Indiana University Dept. of Physics Intermediate Physics Laboratory (P309), http://www.physics.indiana.edu/-dmckinne/p309/ (last modified Nov. 2, 2000).

Ladd, et al., "Reduction of Resonant RF Heating in Intravascular Catheters Using Coaxial Chokes," Abstract from *Magn: Reson. Med.*, 43(4):615-619 (2000).

Liu, et al., "Safety of MRI-Guided Endovascular Guidewire Applications," Abstract from *J. Magn. Reson. Imaging*, 12(1):75-78 (2000).

"Magnetism," xrefer, http://www.xrefer.com/entry/489951 (Aug. 8, 2002).

"The Mean Field Model," http://carini.physics.indiana.edu/P616/lecture-notes/mean-field.html (Aug. 8, 2002).

"The Mean Field Model," http://carini.physics.indiana.edu/P616/lecture-notes/mean-field.html (Jul. 3, 2003).

Nitz, et al., "On The Heating of Linear Conductive Structures As Guide Wires and Catheters in Interventional MRI," Abstract from *J. Magn. Reson. Imaging*, 13(10)105-114 (2001).

"The Nobel Prize in Chemistry 2000," http://www.nobel.se/chemistry/laureates/2000/index.html (Jul. 3, 2003).

"Nobel Prize 2000 for the Discovery and Development of Conductive Polymers," Panipol Conductive Polymers, Panipol Ltd., http://www.panipol.com/ (Jul. 8, 2003).

"About Technology, Definitions, Advantages, Products, Applications, Evaluation, Techn. History, Contact, References," Panipol Conductive Polymers, Panipol Ltd., http://www.panipol.com/noframes.htm (Jul. 3, 2003).

"The Heatsink Guide: Peltier Coolers," http://www.heatsink-guide.com/peltier.htm (Jul. 3, 2003).

Stephens, J., "Peltier CPU Cooling," http://www.pcmech.com/show/processors/140/ (Aug. 13, 2002).

Tellurex Corporation, "Frequently Asked Questions," http://www.tellurex.com/resource/txfaqc.htm (Sep. 16, 2002).

"'TMD' System Overview," Otani, Inc., http://www.otari.com/products/TMD.html (Aug. 8, 2002).

"Types of Magnetism," http://www.physics.hull.ac.uk/magnetics/Magnetism/Types/types.html (Aug. 8, 2002).

"Types of Magnetism," http://www.physics.hull.ac.uk/magnetics/Megnetism/Types/types.html (Jul. 3, 2003).

Wohlgemuth, et al., "Laser-Induced Interstitial Thermotherapy of the Uterus in an Open MRI System: Preliminary In Vitro and In Vivo Experience," http://www.toshiba-medical.co.jp/tmd/review/rv76/r76_6.thm (Jul. 8, 2003).

Farlow's Scientific Glassblowing Inc.'s website (various pages).

International Search Report; PCT US 03/09494, report mailed Jun. 9, 2003.

International Search Report PCT US 03/01203, report mailed Jun. 4, 2003.

Pierce, J. P., Abstract, Table of Contents, and Chapter 1: "Introduction to Magnetic Nanostructures" in "Tailored Magnetic Nanostructures on Surfaces," available at http://web.utk.edu/~jp/thesisJP.htm, May 2003.

U.S. Appl. No. 10/375,719, filed Feb. 25, 2003, Chen, John.

\* cited by examiner

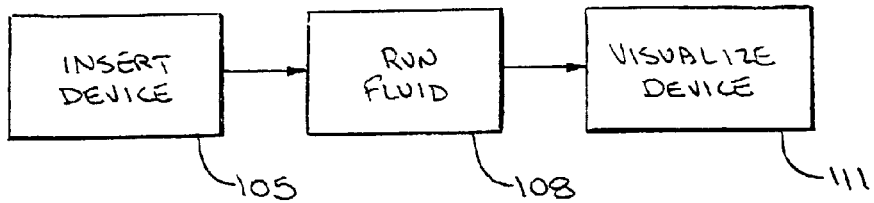
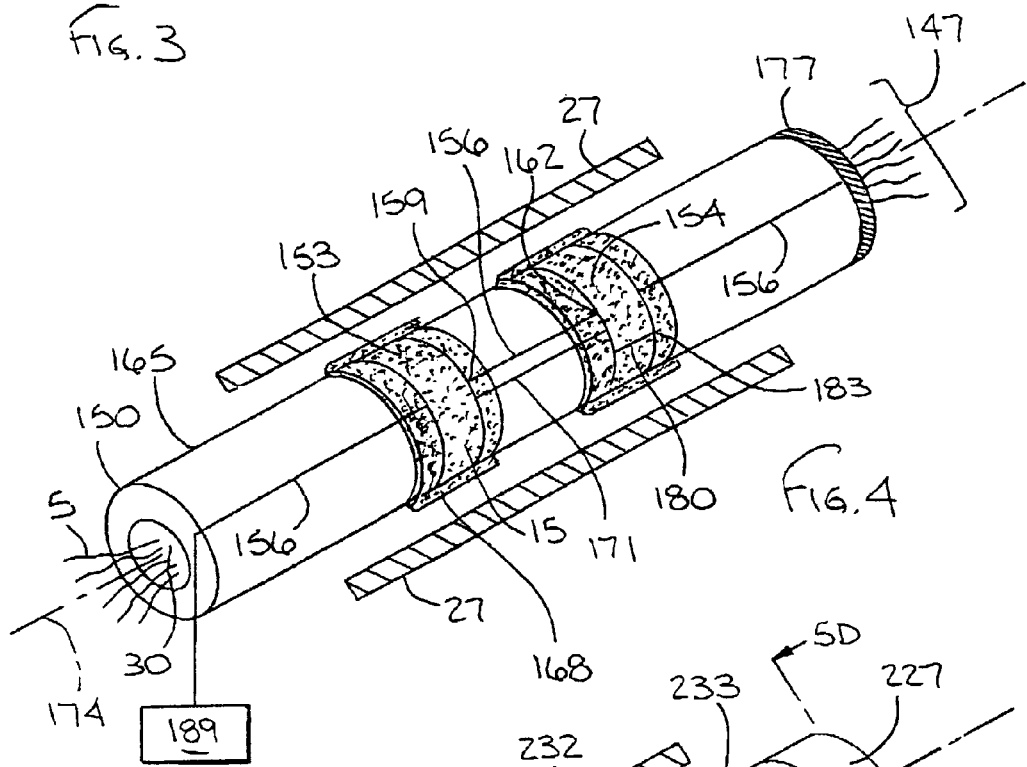
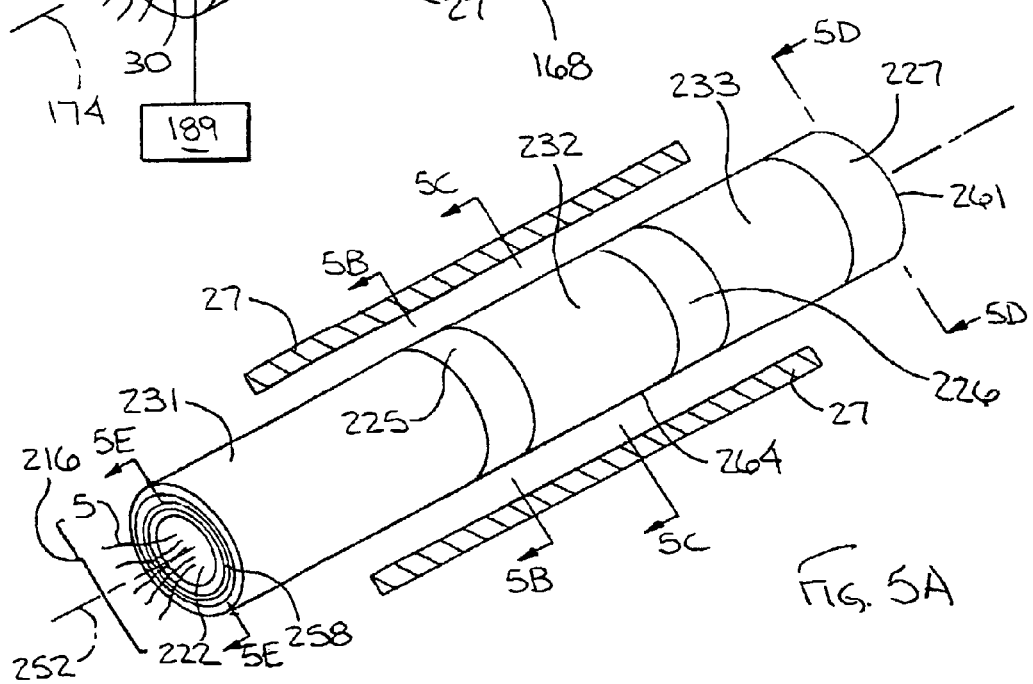

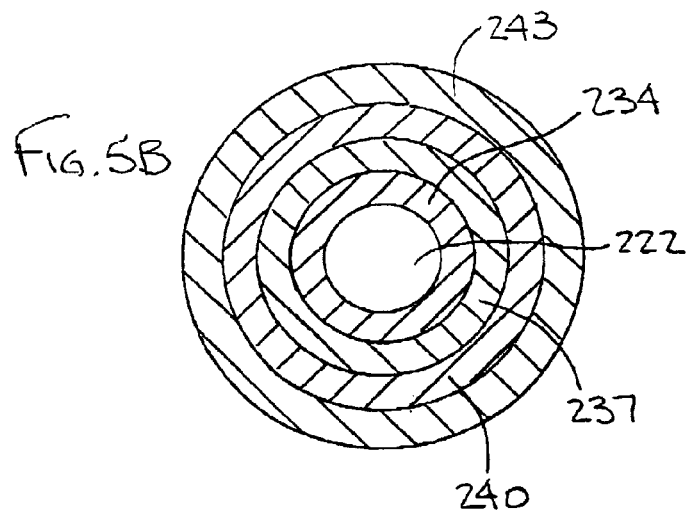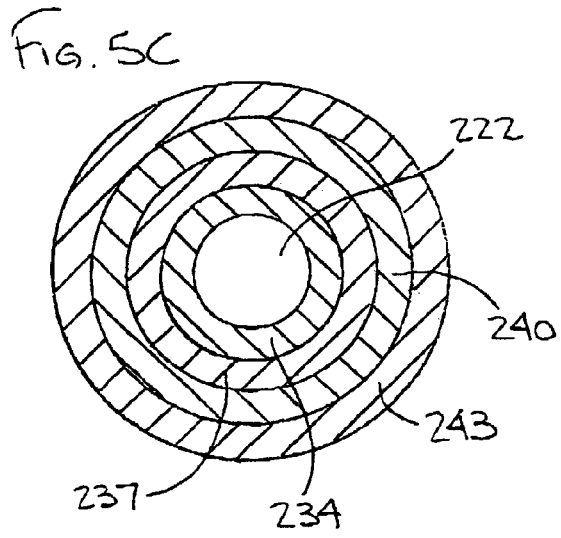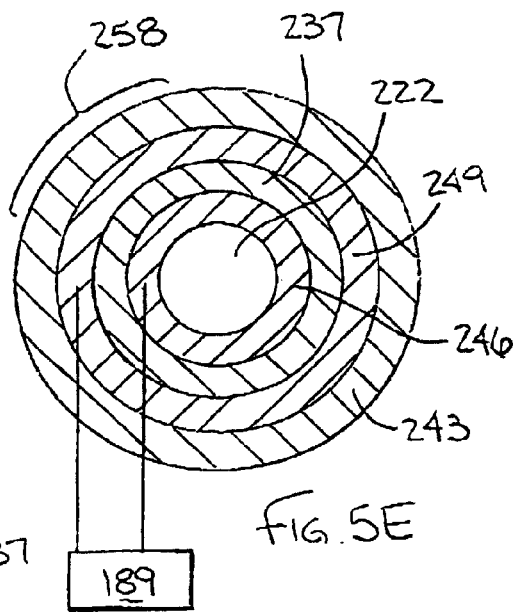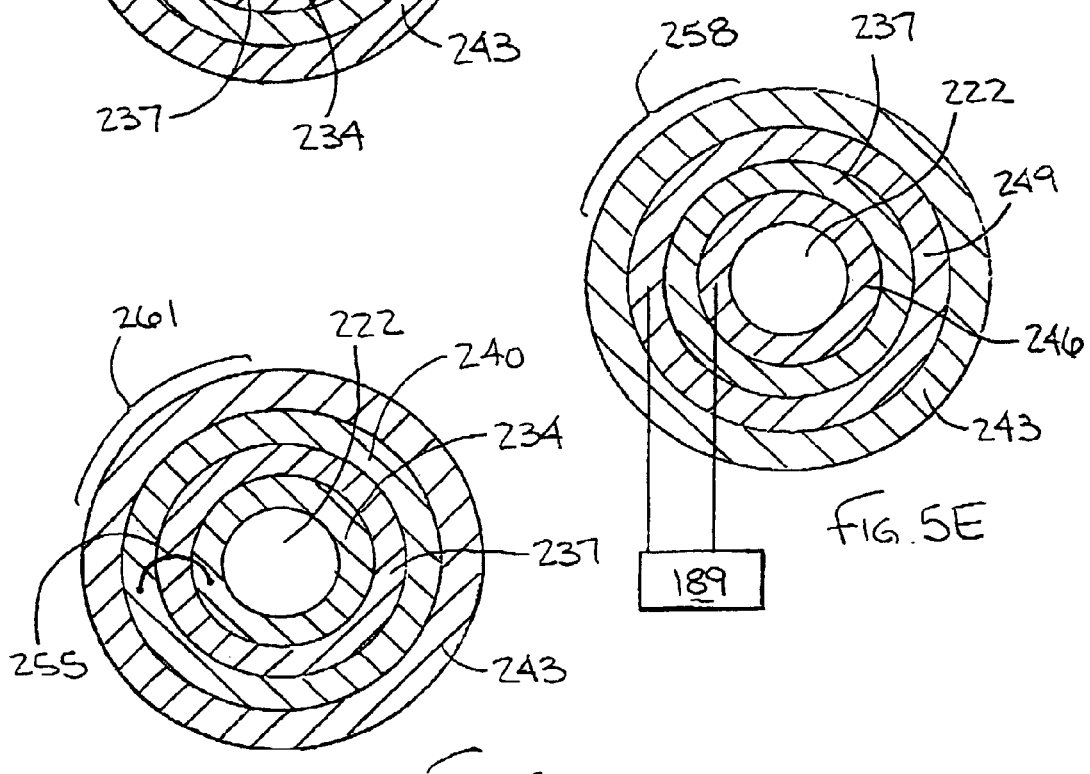

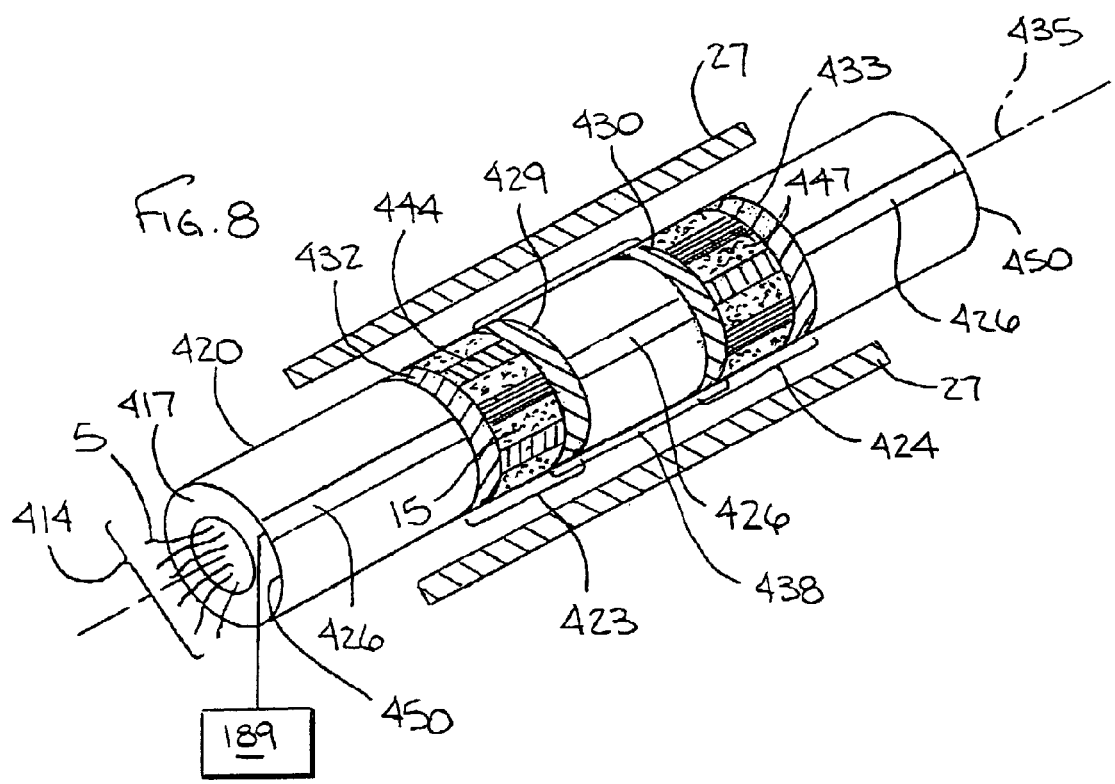

MEDICAL DEVICE WITH TEMPERATURE MODULATOR FOR USE IN MAGNETIC RESONANCE IMAGING

FIELD OF DISCLOSURE

The disclosure generally relates to medical devices and, more particularly, to medical devices having a temperature modulator that allows for manipulation of the magnetic resonance image of the medical device.

BACKGROUND OF THE DISCLOSURE

Pericutaneous transluminal coronary angioplasty (PTCA) and pericutaneous transluminal angioplasty (PTA) have become common, effective procedures for treating blockages within the blood vessels or lumens of the human body. With such procedures, a catheter is navigated through the lumen to the area of blockage whereupon a balloon, navigated through the catheter to the same site, is then inflated to expand the blocked lumen and alleviate flow blockage. In order for the physician to visualize the position to which the catheter and the lumen are navigated, x-ray fluoroscopy technology has typically been employed. More specifically, a radiopaque filler material is typically embedded within the polymer matrix of the balloon and catheter, such that when the body is exposed to x-ray radiation, the radiopaque filler material, which does not transmit the x-ray radiation, becomes clearly visible upon the monitor projecting the x-ray image. Such filler materials typically include salts of barium, tungsten, and bismuth. While effective, such high-level exposures of x-ray radiation to the human body is not desirable.

Another form of imaging available to the medical community, is magnetic resonance imaging (MRI). MRI, a specialized form of nuclear magnetic resonance (NMR), is a spectroscopic technique used to obtain microscopic chemical and physical information about molecules. The radiation emitted due to the change in spin orientation is readable by MRI devices. MRI relies upon the small magnetic field or spin associated with hydrogen nuclei. The spin produces a magnetic field that is readable by MRI devices. Since the human body is comprised of approximately two-thirds hydrogen atoms, if a material is deposited or otherwise introduced into the body that alters this magnetic field or spin, MRI devices can easily identify the area where the material is introduced and thereby identify the location of the material.

MRI is a highly versatile technology that has revolutionized health care. MRI is generally directed at the protons of water and fat molecules. Protons can be thought of as mini-magnets. In the presence of a magnetic field, protons rotate or "precess" around an axis parallel to that field at what is known as the Larmor frequency. A small majority of the protons will align themselves with the main magnetic field as this represents the lowest energy level. When hit with a pulse of radiofrequency radiation that has the same frequency as the Larmor frequency, the protons can absorb this radiation and align themselves opposing the magnetic field at the higher energy level. The subsequent emission signal from the protons when decaying back to the lower energetic level can be detected and used to generate images. MRI involves such parameters as proton density, longitudinal relaxation time (T1), and transverse relaxation time (T2). MRI makes use of the behavior of protons in a magnetic field, a behavior that is influenced by a proton's environment. For example, the protons in hematomas and tumors, can be distinguished from those in normal tissue. Pulse sequences can be designed to be flow sensitive, which makes possible MRI angiography, which provides images of blood flow and the vasculature in general. One specific application of MRI angiography is to follow what brain regions are active when an individual performs particular tasks.

MRI generally requires: a magnet that generates the static magnetic field, shim coils that improve field homogeneity, a radiofrequency (RF) coil that sends the RF pulse, a receiver coil for detection of the emission signal, gradient coils that enable the localization of the emission signal, and a computer and associated software for transforming the data into an image. Proton density, T1 relaxation time, T2 relaxation time, and flow all influence emission signal intensity. The radiofrequency pulse is generally at right angles or transverse to the static magnetic field. After the pulse, the protons return to their normal magnetic state. Specifically, the translational or longitudinal magnetic field (in the direction of the static magnetic field) is restored, and the transverse magnetic field decays. T1 is the measure of longitudinal magnetization's return to its equilibrium state. T2 is the measure of transverse magnetization's return to its equilibrium state. Even though T1 and T2 are simultaneous, they can have very different effects on the final image. T1 and T2 can vary significantly from one tissue to the next, and these differences can be utilized for achieving better contrast.

Image contrast is a major concern in MRI, and there are a number of different approaches to improving contrast. One way of improving contrast is to change the pulse sequence by altering the strength, timing and multiplicity of the RF and gradient pulses. In particular, one can manipulate the time between RF pulses known as the repetition time (TR) and the time between the pulse and the subsequent echo known as the echo time (TE). Alterations in TR and TE can affect T1 and T2. When a pulse sequence is designed to highlight T1, the term T1-weighted imaging is used. T1-weighted imaging employs a short TR to accentuate the T1 effects and short TE to minimize T2 effects. T2-weighted imaging employs a long TR and long TE.

Contrast can be improved by means besides pulse sequence modification. These means include contrast agents, magnetization transfer contrast and diffusion-weighted contrast. Contrast agents generally have some magnetic property associated with them such as ferromagnetism, paramagnetism and superparamagnetism. Ferromagnetism is a characteristic of certain metals, alloys and compounds, wherein internal magnetic moments can permanently adopt a common orientation even after removal of the external magnetic field. Paramagnetism is a characteristic of certain materials, wherein internal moments can temporarily adopt a common orientation as long as supported by an external magnetic field. Superparamagnetism is a characteristic of very small ferromagnetic particles such that they behave as paramagnetic substances due to the loss of permanent magnetization because of normal thermal lattice and molecular vibrations.

The Curie point is the temperature above which a ferromagnetic material becomes paramagnetic. The principle of the Curie point and material that possesses one have been utilized in various technological areas including refrigeration and duplication of magnetic media. Paulus, et al. U.S. Pat. No. 5,429,583 describes the use of cobalt palladium seeds with a Curie point in a therapeutical range for thermal treatment of tumors. Paramagnetic contrast agents include manganese (Mn), gadolinium (Gd), and dysprosium (Dy). These and other contrast agents are sometimes contained within medical devices. Superparamagnetic contrast agents include various iron oxide compounds, as well as in general nano-sized particles containing transition metals including, but not limited to, cobalt, nickel, manganese, and chromium.

Medical devices and various other implants can actually complicate the use of MRI if those implants are magnetically susceptible. Such implants may have been unintentional, e.g. shrapnel, especially when in the eye. Pacemakers and aneurysm clips often rule out the use of MRI. However, in many medical situations, a principal aim may be to visualize an implanted device such as a catheter or stent. Ratner U.S. Pat. No. 4,989,608, Weber et al. U.S. Pat. No. 5,728,079, Young et al. U.S. Pat. No. 5,817,017 and Weber et al. U.S. Pat. No. 5,908,410 all report devices that can be visualized using MRI. There is a need for devices that give the physician, medical technicians and others improved contrast and greater flexibility using MRI to visualize medical devices.

A Peltier element transfers heat by means of electricity from one member to another, causing the former member to cool in the process. A Peltier element is designed such that when a current is applied, both positive and negative charge carriers move from the member to be cooled to the other member. Since each carrier possesses thermal energy, a Peltier element permits heat energy to move against a thermal gradient. Peltier elements have been used in such diverse areas as outer space, submarines, electronics and water coolers.

Conductive polymers are an emerging technology that have generated much attention in recent years including the awarding of the Nobel Prize for chemistry in 2000. Conductive polymers have many potential applications, which include flat screen displays, antistatic devices, catalysts, deicer panels, electrochromic windows, fuel cells and radar dishes. Conductive polymers have already found their way into some medical devices. Examples of conductive polymers include poly-p-phenylenevinylene, and polyanilines such as Panipol®. Other conducting polymers belong to the class of conjugated polymers, which include, but are not limited to the following: poly-pyrrole (PPY), poly-aniline, poly-thiophene (PtH) and paraphenylene vinylene (PPV). Further improvements can be obtained with doping of metallic elements within the polymer matrix. The conductivity of conductive polymers can be designed to be anywhere between non-conducting to metallic conducting, and can be blended with PE, PVC and many other polymers. Conductive polymers are also amendable to a wide variety of processing techniques including extrusion and injection molding.

While heating and cooling elements have been employed in medical devices, including catheters, such elements have been used principally for tissue destruction, patient warming, measuring blood flow and as a means of controlling the movement of a device. The medical community needs new methods of detecting devices using MRI, new medical devices whose visualization by MRI may be manipulated and new methods of manufacturing such medical devices. The present disclosure addresses that need by employing heating, cooling and magnetic materials to provide novel devices, methods of use and methods of construction that will deliver positive health benefits.

SUMMARY OF THE DISCLOSURE

In accordance with one aspect of the disclosure, a medical device is provided, which is adapted to be inserted into tissue and to be located using a magnetic resonance imaging device. The medical device includes a housing. A temperature modulator, which serves to alter the magnetic resonance image of the medical device, is operatively associated with the housing. A hydrophilic layer is operatively associated with at least a portion of the housing. A material that possesses a Curie point is operatively associated with the medical device.

In accordance with another aspect of the disclosure, a method is provided. The medical device comprises a housing, and a temperature modulator, the temperature modulator being operatively associated with the housing. First, the medical device is inserted into a subject. Next, a temperature of the medical device is modulated so that the temperature of at least part of the medical device is altered so as to modify the detectability of the medical device via magnetic resonance imaging. After that the medical device is visualized using magnetic resonance imaging.

In accordance with another aspect of the disclosure, another method is provided. This method involves first inserting a medical device into tissue, wherein the medical device comprises a housing and at least one lumen, the lumen being operatively associated with the housing, and able to accept a fluid. Next, a fluid is run through one or more the lumens so as to affect the visibility of the medical device using MRI. After that the medical device is visualized using MRI.

In accordance with another aspect of the disclosure, a medical device is provided, which is adapted to be inserted into tissue and to be located using a magnetic resonance imaging device. The medical device includes a housing and bands, composed of a conductive material being operatively associated with the housing, arranged along a longitudinal axis of the medical device. There is also present a conductive material for connecting the bands to each other and to a current source, such that the conductive material composing the bands has a higher resistivity than the conductive material connecting the bands to each other and to a current source.

In accordance with another aspect of the disclosure, a medical device is provided, which is adapted to be inserted into tissue and to be located using a magnetic resonance imaging device. The medical device includes a lumen and a housing surrounding the lumen. The housing includes first, second and third layers. The first layer surrounds the lumen, the second layer surrounds the first layer, and a third layer surrounds the second layer. The first and third layers comprise a conductive polymer. The second layer comprises a conductive polymer with a resistivity higher than the conductive polymer of the first and third layers in each heating region, and the second layer comprises an isolating material in the non-heating regions. There is at least one heating region along a longitudinal axis of the medical device. There is also a means for completing the electrical circuit between the first layer and the third layer on a distal end of the medical device. A first conductive ring or positioned over the first layer, and a second conductive ring placed over the third layer at a proximal end of the medical device so as to allow connection to an external source of electricity. Conductive rings that are a part of this disclosure can be comprised of metal, conductive polymers or combinations thereof.

In accordance with another aspect of the disclosure, a method for imaging a medical device is provided. This medical device comprises the housing, bands composed of a conductive material being operatively associated with the housing, arranged along a longitudinal axis of the medical device, and a conductive material for connecting the bands to each other and to a current source. The conductive material composing the bands has a higher resistivity than the conductive material connecting the bands to each other and to a current source. This method first involves inserting the medical device into a subject. Next, electric current is passed through the medical device so as to heat at least part of the medical device above body temperature to see a sufficient effect (contrast) on a MRI. The current in the medical device is then ceased and the medical device is visualized using MRI.

In accordance with another aspect of the disclosure, a method for imaging a medical device is provided. The medical device comprises a housing, bands composed of a conductive material operatively associated with the housing, arranged along a longitudinal axis of the medical device, and a material that possesses a Curie point above body temperature, the material being operatively associated with the housing. A first step in the method is to insert the medical device into a subject. Next, a radiofrequency pulse is emitted so as to heat at least part of the medical device above body temperature to see a sufficient effect (contrast) on a MR image. After that the radiofrequency pulse is ceased and the medical device is visualized using MRI.

In accordance with another aspect of the disclosure, a medical device is provided, which is adapted to be inserted into tissue and to be located using a magnetic resonance imaging device. The medical device comprises a housing, at least one Peltier element, each Peltier element being operatively associated with the housing, a means of connecting the Peltier elements to each other and a power source, and a hydrophilic layer operatively associated with the housing.

In accordance with another aspect of the disclosure, a medical device is provided, which is adapted to be inserted into living tissue and to be located using a magnetic resonance imaging device. This medical device comprises a lumen and a housing surrounding the lumen. The housing includes first, second and third layers. The first layer surrounds the lumen, the second layer surrounds the first layer, and a third layer surrounds the second layer. There is at least one Peltier element arranged along a longitudinal axis of the medical device. The first layer comprises a conductive polymer, the second layer comprises an isolating layer, the third layer comprises at least one Peltier element and at least one stripe of conducting polymer connecting the Peltier elements to each other and to an external source of electricity. Each Peltier element has a relatively cold region and a relatively hot region, wherein Peltier elements are arranged so that the hot region of one Peltier element does not face the cold region of an adjacent Peltier element. Each Peltier element comprises alternating n-type and p-type semiconductor segments arrayed around a perimeter of the medical device, and contained within the third layer of the medical device.

In accordance with another aspect of the disclosure, a method for imaging a medical device is provided. The medical device comprises a housing, at least one Peltier element, each Peltier element being operatively associated with the housing, and a means of connecting the Peltier elements to each other and a power source. The method comprises inserting the medical device into a subject, passing electric current through the medical device so as to cool at least a portion of the medical device relative to body temperature in order to see a sufficient effect (contrast) on a MRI, ceasing the flow of current in the medical device and visualizing the medical device using MRI.

In accordance with another aspect of the disclosure, a method of manufacturing a medical device is provided, which includes extruding two stripes of conducting polymer along a longitudinal axis of the medical device, each of the stripes covering a metal wire that also runs along the longitudinal axis of the catheter, and then removing the wire in those sections where a band (heating element) is desired to be located.

In accordance with another aspect of the disclosure, a method of manufacturing a medical device is provided. At least two stripes of conducting polymer are extruded along a longitudinal axis of the medical device. The conductive polymer is then removed in those sections where an electro-active temperature modulator element is to be located. Electro-active temperature modulator elements are inserted in those areas where the conductive polymer has been removed.

These and other aspects and features of the disclosure will become more readily understood by reference to the following detailed description when taken in conjunction with the accompanying drawings.

BRIEF DESCRIPTION OF THE DRAWINGS

FIG. 3 is a flow chart depicting a method for imaging a medical device in accordance with the teachings of this disclosure.

FIG. 4 is a perspective view of a medical device, constructed in accordance with the teachings of this disclosure, comprising a housing, bands of conductive material, and conductive material for connecting said bands.

FIG. 5A is a perspective view of a medical device, constructed in accordance with the teachings of this disclosure, which comprises four layers, a lumen, a first layer surrounding the lumen, at least one heating region along a longitudinal axis, a means for completing the electrical circuit between the first layer and the third layer on the distal end of the medical device, and two conductive rings at the proximal end of the medical device so as to allow connection to an external source of electricity.

FIG. 5B is an enlarged sectional view of the medical device depicted in FIG. 5A and taken along line 5B-5B of FIG. 5A.

FIG. 5C is an enlarged sectional view of the medical device depicted in FIG. 5A and taken along line 5C-5C of FIG. 5A.

FIG. 5D is an enlarged sectional view of the medical device depicted in FIG. 5A taken along line 5D-5D of FIG. 5A.

FIG. 5E is an enlarged sectional view of the medical device depicted in FIG. 5A taken along lie 5E-5E of FIG. 5A.

FIG. 8 is a perspective view of a medical device, constructed in accordance with the teachings of this disclosure, which comprises a housing, at least one Peltier element, a means of connecting said Peltier elements together, and a hydrophilic layer.

Figure 1:
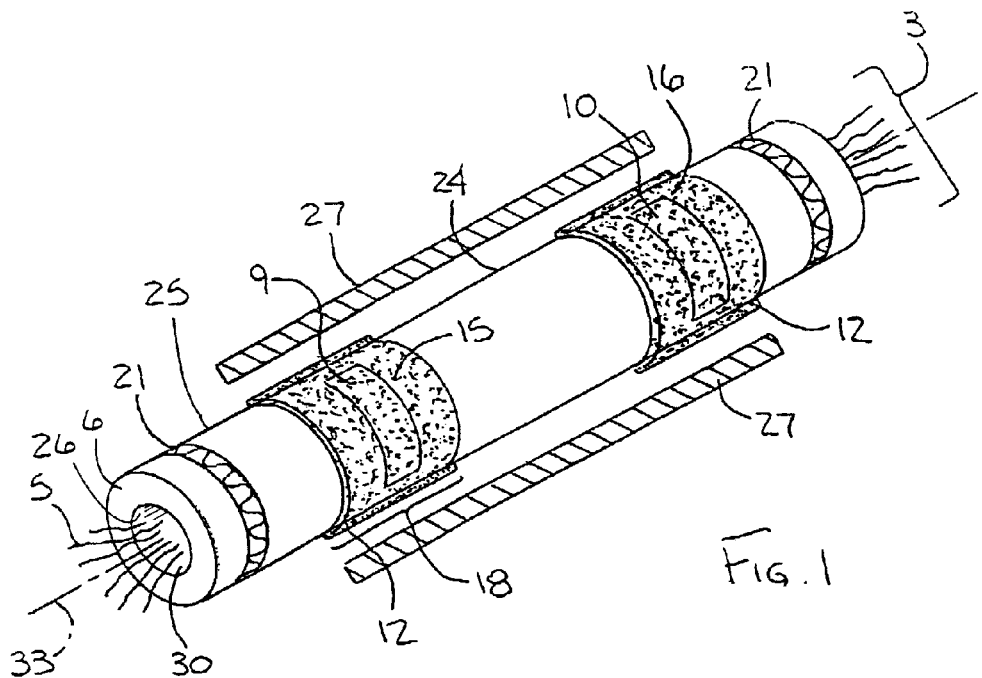
FIG. 1 is a perspective view of a medical device, constructed in accordance with the teachings of this disclosure, comprising a housing, a temperature modulator, a hydrophilic layer, and a material that possesses a Curie point.

While the disclosure is susceptible to various modifications and alternative constructions, certain illustrative embodiments thereof have been shown in the drawings and will be described below in detail. It should be understood, however, that there is no intention to limit the disclosure to the specific forms disclosed, but on the contrary, the intention is cover all modifications, alternative constructions, and equivalents falling within the spirit and scope of the disclosure as defined by the appended claims.

DETAILED DESCRIPTION

Referring now to the drawings, and with special reference to FIG. 1, a medical device constructed in accordance with the teachings of the disclosure is generally referred to by reference number 3. The medical device 3 is adapted to be inserted into tissue and to be located using a magnetic resonance imaging (MRI) device 27. In FIG. 1, the medical device 3 is represented as having a generally tubular shape such as that of a catheter or stent. However, the teachings of the disclosure can be used in conjunction with other types of medical devices, including, but not limited to guidewires, sheath introducers and biopsy needles. The medical device as shown is for illustrative purposes only. Nevertheless, those embodiments in which the medical device is a catheter will generally include a lumen 30, through which a liquid 5 may flow.

As shown in FIG. 1, the medical device 3 may include a housing 6, a first temperature modulator 9, a hydrophilic layer 12, and a material 15 that possesses a Curie point. In some embodiments, the medical device 3 may also include radiopaque material 21, which allows the medical device 3 to be visible using techniques utilizing x-rays. All medical devices and methods of using medical devices in this disclosure are understood to be capable of including embodiments comprising radiopaque material 21 in any number of different patterns and arrangements.

While the device 3 in FIG. 1 is shown with the first temperature 9 modulator and a second modulator 10, the medical device 3 may include at least a first temperature modulator 9 or a greater number of temperature modulators as well. In certain embodiments, the first temperature modulator 9 will be capable of causing an increase or decrease in the temperature of all or part of the medical device 3. In some embodiments, a first temperature modulator 9 will be able to increase the temperature of all or part of the medical device 3, and the second temperature modulator 10 will be able to decrease the temperature of all or part of the medical device 3. In FIG. 1, the temperature modulator is shown affecting the temperature of a temperature zone 18, but that is for illustrative purposes only. Temperature modulators, e.g. reference numbers 9 and 10 in FIG. 1, can take on different types, shapes and placements, and those shown in FIG. 1 are only representative and illustrative. In fact, the lumen 30 and accompanying fluid 5, may also serve as a temperature modulator. As explained below, temperature modulators can include, but are not limited to, Peltier elements, heating bands and systems employing gas expansion. Such gas expansion systems use a gas flowing through a first lumen, which is then expanded and returns through a second, wider lumen. In general, a temperature modulator is understood to be a component capable of creating a temperature differential with its environment.

In FIG. 1, the hydrophilic layer 12 is shown covering only a portion of an outer surface 25 of the housing 6, but the hydrophilic layer 12 may cover different parts of the surface 24, all of the surface 24, or be absent altogether. The hydrophilic layer also need not be located on the surface 24 of the housing 6. The hydrophilic layer comprises hydrophilic material, and may contain other elements including, but not limited to, water, paramagnetic material, superparamagnetic material, and material 15 that possesses a Curie point. Hydrophilic material may also be found elsewhere in the medical device in other embodiments. In some embodiments, the hydrophilic layer 12 comprises a hydrogel. Unless stated to the contrary, a hydrophilic layer 12 is generally understood to include embodiments where the hydrophilic layer comprises a hydrogel. While the hydrophilic layer 12, when located on the surface 24, may be located anywhere on the surface 24, in some embodiments the hydrophilic layer 12 will be found on the outer surface 25. In some embodiments, the hydrophilic layer 12 will be found on an inner surface 26. Certain embodiments may also lack a hydrophilic layer 12.

Generally, the thicker the hydrophilic layer 12, the greater the number of protons that will be affected during magnetic resonance imaging, and the more signal distortion in the average voxel signal. In some embodiments, the affected protons may be within the housing 6 of the medical device 3. One making use of the medical device 3, and other embodiments taught by this disclosure, will appreciate that the thinner the hydrophilic layer 12, the greater the temperature difference has to be to have an effect on the average voxel temperature. While there is no real limit to the thickness of the hydrophilic layer 12, one will appreciate that the thickness of the hydrophilic layer 12 may be limited by the size of the body cavity into which the medical device 3 will be placed as well as the size of the medical device 3. In some embodiments, the hydrophilic layer is 0.1 mm thick. In some embodiments, the hydrophilic layer is from 0 to 5 mm thick. In some embodiments, the hydrophilic layer is from 0 to 1 mm thick. In some embodiments the hydrophilic layer is from 0.05 to 0.5 mm thick. One will also appreciate that the hydrophilic layer 12 may expand or contract depending on its environment, thus affecting the thickness of the hydrophilic layer 12. While the hydrophilic layer 12 has been discussed in relation to medical device 3, in general this same description of the hydrophilic layer 12 is applicable to the other embodiments of this disclosure as well.

In FIG. 1, the medical device 3 is shown as containing material 15 possessing a Curie point. The material 15 may possess a Curie point either above or below body temperature. Body temperature is understood to be 37° C. on average for humans. What body temperature is in a given embodiment will depend on, but is not limited to, such factors as where in the body the medical device is positioned, disease states, the kind (species) of subject into which the medical device is placed, and the type of temperature modulators employed in the medical device. In some embodiments, a first material 15 with a Curie point above body temperature, and a second material 16 with a Curie point below body temperature, or vice versa, may be used, or both may be above body temperature, or both below. In a given embodiment there may be any given number of materials, e.g. 15, 16, that possess a Curie point and each one is capable of possessing a unique Curie point. Curie point in this disclosure is considered to be that temperature below which a material becomes ferromagnetic, and above which ceases to be come ferromagnetic, though it is also understood that the ferromagnetic transition may in actuality take place over a temperature range, rather than at a discrete temperature, and as such Curie points in the disclosure may be taken as midpoints or averages.

The material with a Curie point, e.g. 15 and 16, may be distributed in any configuration and in either part or all of the medical device 3 including, but not limited to, the housing 6 and the hydrophilic layer 12. In FIG. 1, the first material 15 with a Curie point is located in temperature zone 18 and hydrophilic layer 12, but this is for illustrative purposes only, as the material 15 may be located in any of a number of different areas of the medical device 3. The material 15 with a Curie point may be located in any number of a different patterns in the medical device 3. Depending on the particular embodiment, there may be multiple patterns and positions of the material 15, and a particular region may have material 15 with the same or varying Curie point. Moreover, the material 15 in one region may have the same or different Curie point as that in a different region.

The Curie point material 15 may have a Curie point of any temperature, which an individual would desire. Some embodiments will possess a material 15 with a Curie point that falls in the range of 25 and 50 degrees Celsius. Some embodiments will possess a material 15 with a Curie point that falls in the range of 32 and 42 degrees Celsius. Some embodiments will possess a material 15 with a Curie point that falls in the range of five degrees higher and five degrees lower than body temperature. Some embodiments will have a material 15 that possesses a Curie point that comprises at least one element selected from the group consisting of cobalt, palladium, nickel, silicon, chromium, iron, manganese and copper, so as to achieve a desired Curie point. Oxides and other chemical variants of these metals are also understood to be within the scope of the disclosure.

Figure 2:
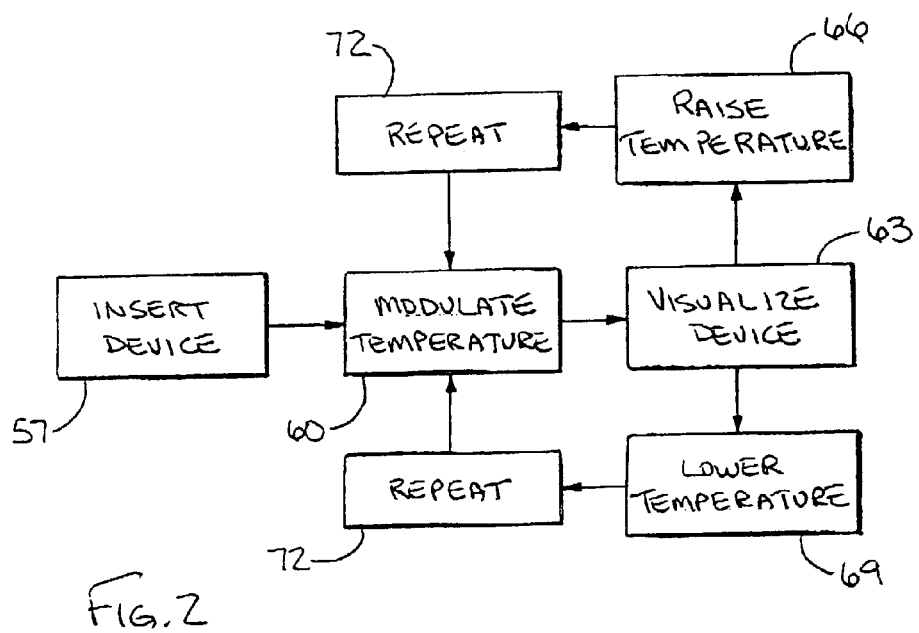
FIG. 2 is a flow chart depicting a method for imaging a medical device in accordance with the teachings of this disclosure.

FIG. 2 outlines a general method according to the disclosure for detecting a medical device 3 that has been inserted into a subject. The medical device, e.g. 3, which is the focus of the method, may comprise a housing 6, and a temperature modulator 9, the temperature modulator 9 being operatively associated with the housing 6. A first step, as indicated by reference number 57, may be to insert the medical device 3 into a subject (not shown). Next, as indicated by reference number 60, a temperature of the medical device 3 is modulated so that the temperature of at least part of the medical device 3 is altered so as to modify the detectability of the medical device 3 via magnetic resonance imaging. After that, as indicated by reference number 63, the medical device 3 is visualized using magnetic resonance imaging. This method may be applied to the medical device 3, illustrated in FIG. 1, however, it may also be applied to other medical devices as well. This method is discussed in reference to medical device 3 for illustrative purposes only.

Many other embodiments of the method represented in FIG. 2 also exist, some of which are discussed below. In some embodiments, the modulating step 60 alters a temperature of the hydrophilic layer 12, operatively associated with the housing 6. In some embodiments, the modulating step 60 decreases the temperature of the hydrophilic layer 12. In some embodiments, the modulating step 60 decreases the temperature of the hydrophilic layer 12 at least one degree Celsius. In some embodiments, the modulating step 60 increases the temperature of the hydrophilic layer 12. In some embodiments, the modulating step 60 increases the temperature of the hydrophilic layer 12 at least one degree Celsius.

In some embodiments, the modulating step 60 further utilizes the material 15 with a Curie point. As indicated above, the material 15 may have a Curie point that is below body temperature. In some embodiments, the modulating step 60 results in the material 15 becoming ferromagnetic. In other embodiments, the modulating step 60 further comprises an additional modulation step 66 following the visualization step 63, comprising raising the temperature of the medical device above the Curie point so that the material is again not ferromagnetic. The raising of the temperature may be performed actively or passively or may include both active and passive temperature change.

The modulating step 60 may further utilize a material 15 having a Curie point that is above body temperature, and in some embodiments, the modulating step 60 may result in the material no longer being ferromagnetic. The modulating step 60 may further comprise an additional modulation step 69 following the visualization step 63, wherein the temperature of the medical device 3 is lowered below the Curie point so that the material 15 becomes ferromagnetic again. The lowering of the temperature may be performed actively or passively or may include both active and passive temperature change.

In some embodiments, the method will include an additional step 72 following additional modulation step 66 or 69, wherein the method is repeated beginning with the modulating step 60.

For the method depicted in FIG. 2, and for all methods according to the teachings of this disclosure, it is contemplated that one may perform additional steps between the described steps, perform additional steps prior to the described steps, as well as perform additional steps after the described steps. One may also alter the order of the described steps and still fall within the teachings of the disclosure. Additionally, one may repeat individual or series of steps. Furthermore, while a given method may refer to a particular medical device, e.g. 3, that is for illustrative purposes only, as performing the method in conjunction with other medical devices is also contemplated. The description of how materials, e.g. 15, 16, with a Curie point may be used in conjunction with a medical device 3, as well as the qualitative nature of those materials, also apply to the methods described in relation to FIG. 2, those methods described below, and all other methods taught by this disclosure.

FIG. 3 outlines another general method according to the disclosure for detecting a medical device 3 that has been inserted into a subject. First, as indicated by reference number 105, the medical device 3 is inserted into tissue (of a subject), wherein the medical device 3 may comprise a housing 6 and at least one lumen 30, the lumen being operatively associated with the housing and able to accept a fluid 5. Next, as indicated by reference number 108, fluid is run through one or more of the lumens, e.g. 30, so as to affect the visibility of the medical device 3 using MRI. After that, as indicated by reference number 111, the medical device 3 is visualized using magnetic resonance imaging.

In some embodiments of the method represented in FIG. 3, the running fluid step 108, further comprises modulating the temperature of the fluid 5 so as to cause an increase or decrease of a temperature of at least part of the medical device 3. In some embodiments, the fluid 5 is run through the lumen 30 so as to lower the temperature of at least part of the medical device 3 below the Curie point of a material 15 in the medical device 3 so that the material 15 becomes ferromagnetic. In some embodiments, the fluid 5 is run through the lumen 30 so as to raise the temperature of at least part of the medical device above the Curie point of a material 15 in the medical device 3 so that the material 15 is no longer ferromagnetic.

FIG. 4 shows another medical device 147 according to this disclosure. The medical device 147 is adapted to be inserted into tissue and to be located using a magnetic resonance imaging device. The medical device 147 may comprise a housing 150, bands, e.g., 153 and 154, composed of a conductive material being operatively associated with the housing 150, arranged along a longitudinal axis 174 of the medical device 147, and a conductive material 156 for connecting the bands, e.g. 153, 154, to each other and to a current source 189. The conductive material 156 composing the bands 153, 154, may have a higher resistivity than the conductive material 156 connecting the bands 153, 154, to each other and to a current source 189.

In some embodiments, the medical device 147, the conductive material 156 connecting the bands 153, 154 to each other and to a current source, comprises non-ferromagnetic metal, including, but limited to silver, copper and gold, wires not more than 7 cm in length 171 and a marker 177 positioned so as to form/complete an electrical loop (circuit). In some embodiments, the medical device 147, the conductive material composing the bands 153, 154, and the conductive material 156 connecting the bands 153, 154 to each other and to a current source both comprise a conductive polymer. All types of conductive polymers are contemplated. Such conductive polymers include, but are not limited to, poly-p-phenylenevinylene, and polyanilines such as Panipol®, and conjugated polymers such as poly-pyrrole (PPY), poly-aniline, polythiophene (PtH) and paraphenylene vinylene (PPV). Further improvements can be obtained with doping of metallic elements within the polymer matrix.

In some embodiments, the medical device 147, shown in FIG. 4, includes bands 153, 154 of a width 180 sufficient to cover about two voxels in a magnetic resonance image with minimal voxel size taken to be approximately 0.64 mm$^3$, i.e. a cube with sides of approximately 0.4 mm. A voxel refers to a volume element in MRI. Magnetic resonance images comprise picture elements called pixels. The intensity of a pixel is proportional to the nuclear magnetic resonance (NMR) signal intensity of a voxel's content of an imaged object. The width 180 is defined as the distance between one edge 162 of the band 154, and another edge 183 of the band 154, with the understanding that the width 180 of the band 154 may vary. In some embodiments the width 180 can be from 0.8 mm to 10 mm. In some embodiments the width 180 can be from 1 mm to 10 mm. In some embodiments the width 180 can be from 0.8 mm to 3 mm. In some embodiments the width 180 can be from 0.8 mm to 4 mm. In some embodiments the width 180 can be from 3 mm to 10 mm. Bands 180 of 3 or 4 mm or even 10 mm in width 180 provide for a larger thermal mass and minimize image noise.

In some embodiments, the medical device 147 shown in FIG. 4 includes bands 153, 154 spaced apart at a distance 171 between 3 millimeters and 15 millimeters, but narrower and wider distances 171 are also contemplated. The distance 171 is defined as the length between the edge 159 of one band 153 and the edge 162 of the adjacent band 154, with the understanding that the distance 171 may vary.

In various embodiments, it is understood that the medical device 147 shown in FIG. 4, may include a hydrophilic layer 168 on at least a portion of a surface of the medical device 147. Hydrophilic layer 168 shown in FIG. 4 is analogous to hydrophilic layer 12 of medical device 3 shown in FIG. 1. Moreover, medical device 147 can possess all the variations and elements described above for medical device 3. For example, the medical device may include a material 15 with a Curie point, analogous to the material, e.g. 15, 16, show in FIG. 1 for medical device 3. For illustrative purposes only, the material 15 that possesses a Curie point is shown within and around the heating bands, e.g. 153, 154, and within the hydrophilic layer 168.

FIGS. 5A, 5B, 5C, 5D, and 5E show a medical device 216, according to the disclosure, which is adapted to be inserted into tissue and to be located using a magnetic resonance imaging device, and may include a lumen 222, through which a fluid 5 may flow through. The medical device includes a housing 219, which surrounds a lumen 222. As visible in FIGS. 5B, 5C, and 5D, the housing 219 includes three layers: a first layer 234 surrounding the lumen 222, a second layer 237 surrounding the first layer 234, a third layer 240 surrounding the second layer 237. A fourth layer 243 surrounds the third layer 240, but is not part of the housing. The medical device 216 also includes at least one heating region, e.g., 225, 226 and 227, along a longitudinal axis 252 of the medical device 216. FIG. 5D shows that the medical device 216 also includes a means 255 for completing a electrical circuit between the first layer 234 and the third layer 240 on the distal end 261 of the medical device 216.

As shown in FIG. 5E, a first conductive ring 246 is positioned over the first layer 234 and a second conductive ring 249 placed over the third layer 240 at the proximal end 258 of the medical device 216 so as to allow connection to a current source 189. The first layer 234 and third layer 240 comprise a conductive polymer. The second layer 237 comprises a conductive polymer with a resistivity higher than the conductive polymer of the first layer 234 and third layer 240 in each heating region, e.g. 225, 226 and 227. The second layer 237 comprises an isolating (insulating) material in the non-heating regions, e.g. 231, 232 and 233. Isolating/insulating materials that may be used include, but are not limited to, non-conducting polymers. Some embodiments employ polymers such as pebax 72D, Nylon 12, pellethane, PTFE, HDPE, which provide the stiffness and other mechanical properties required of a standard catheter.

The medical device 216 shown in FIGS. 5A-E further comprises a fourth layer 243 surrounding the third layer 240, wherein the fourth layer 243, a hydrophilic layer, comprises a hydrophilic material such as a hydrogel. Although depicted as covering the entire third layer 240, it is to be understood that the fourth layer 243 may cover all or part of the surface 264 of the housing 219. In other embodiments, the hydrophilic layer 243 may be located elsewhere in the medical device 216. The fourth layer 243 comprising hydrophilic material shown in FIG. 5A-E is analogous to hydrophilic layer 12 of medical device 3 shown in FIG. 1. Moreover, medical device 216 can possess all the variations and elements described above for medical device 3.

Figure 6:
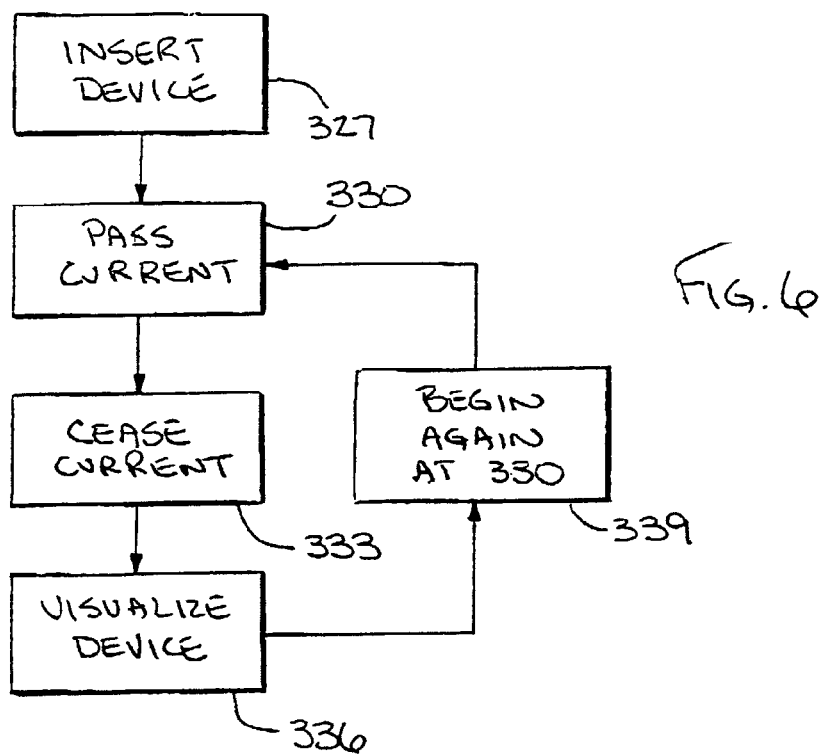
FIG. 6 is a flow chart depicting a method in accordance with the teachings of the disclosure.

FIG. 6 represents a method according to the disclosure for imaging a medical device, e.g. 147 as described above, within a subject. Examples of such a medical device are shown in FIGS. 4, 5A-5E. The method represented in FIG. 6 comprises the following steps. First, the medical device, e.g. 147, is inserted into a subject, as indicated by step 327. Next, in a step 330, electric current is passed through the medical device, e.g. 147, so as to heat at least part of the medical device, e.g. 147, above body temperature to see a sufficient effect (contrast) using a MRI device. After that, in step 333, the current traversing through the medical device, e.g. 147, is ceased. Then, in step 336, the medical device, e.g. 147, is visualized using MRI.

In some embodiments, the method represented in FIG. 6, comprises an additional step 339 of returning to the step 330 and repeating the method from that step. In such embodiments the resulting cycle can be repeated as many times as is necessary to produce the desired image quality. In some embodiments, the passing current step 330 further comprises heating a hydrophilic layer, e.g. 168, of the medical device, e.g. 147. In some such embodiments, the hydrophilic layer, e.g. 168, may be heated to at least 41° C.

Ferromagnetic materials are materials, which, upon exposure to an alternating magnetic field, vibrate at the frequency of the applied field. Due to such vibration, material, or material upon which the ferromagnetic material is embedded or attached, is heated due to the hysterisis losses associated with the vibration. Moreover, the ferromagnetic materials are not only heated, but are heated only to a constant temperature known as the Curie temperature (point) of the material, whereupon the vibrations cease and the material begins to cool. Accordingly, if such a ferromagnetic material is provided on, or embedded within, a medical device, and the device is then subjected to an alternating magnetic field, such as that generated by the magnetic resonance imaging device, the medical device will elevate in temperature. This elevation in temperature will then be visible via the magnetic resonance imaging equipment. The imaging can be enhanced by incorporating the ferromagnetic material within a hydrophilic layer such as a hydrogel, which is then adhered or otherwise attached to the housing of a medical device.

The radio frequency pulse sequence of the MRI device can be alternated, i.e. switched on and off to alter the visibility of the device. During the radiofrequency field "on" status there is no image. Therefore, it would be proposed that a pulse sequence would be used which alternately turns the radio frequency coil on and off to heat the device followed by an "off" period to gather the magnetic resonance signals. While such a pulse sequence is generally employed in MRI, this disclosure teaches the unique practice of designing the pulse sequence to have a prolonged "on" period so as to heat the material with a Curie point sufficiently.

Figure 7:
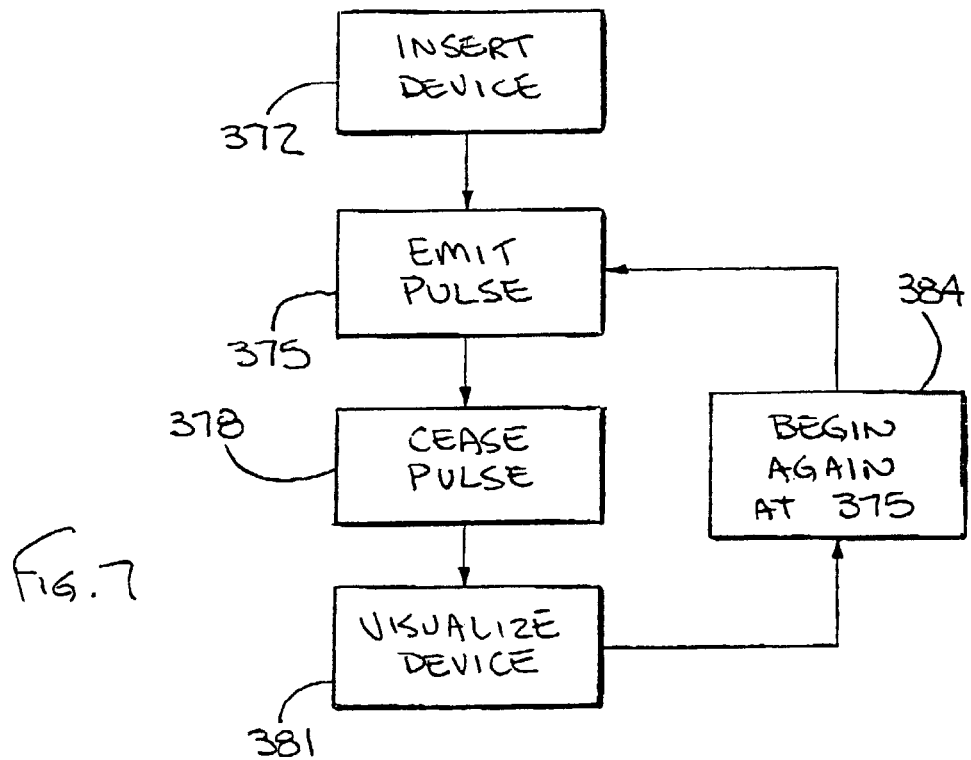
FIG. 7 is a flow chart depicting another method in accordance with the teachings of the disclosure.

FIG. 7 represents a method according to the disclosure for visualizing a medical device in a subject. The method involves a medical device, similar to 147, but lacking the direct current source 189 and connecting elements 156, marker 177 along with any other necessary modifications. The medical device comprises a housing 150, bands, e.g. 153, 154 composed of a conductive material being operatively associated with the housing 150, arranged along a longitudinal axis 174 of the medical device 147, and a material 15 that possesses a Curie point above body temperature, the material 15 being operatively associated with the housing 150. The method may include a first step 372 of inserting the medical device, e.g. 147, into a subject. Next, in a step 375, a radiofrequency pulse is emitted so as to heat at least part of the medical device 147 above body temperature to see a sufficient effect (contrast) on a MR image. After that, in a step 378, the radiofrequency pulse is ceased. Then, in a step 381, the medical device 147 is visualized using MRI.

In some embodiments, the method represented in FIG. 7, further comprises an additional step 384 of repeating the method at the emitting step 375. In some embodiments of the method shown in FIG. 7, the sending step 375 further comprises a hydrophilic layer 168, such as a hydrogel, on all or part the surface 165 of the housing 150 In such embodiments, the inserting step 372 utilizes a housing 150, which is composed of a polymer, and the material 15, that possesses a Curie point, is 0% to 5% by weight of the medical device 147, with modifications as discussed above, in those areas of the medical device 147 possessing the material 193. The hydrophilic layer may also include a material 15 with a Curie point.

FIG. 8 depicts a medical device 414 which is adapted to be inserted into tissue and to be located using a magnetic resonance imaging device 27. The medical device 414 comprises a housing 417, a surface of the housing 420, at least one Peltier element 423, 424, each Peltier element being operatively associated with the housing 417. A means 426 of connecting the Peltier elements 423, 424 to each other and a power source 189, and a hydrophilic layer 438 operatively associated with the housing 417 are also provided.

In some embodiments, the medical device 414 is constructed such that each Peltier element 423, 424 includes a hot region, 432, 433, and a cold region 429, 430, whereby the Peltier elements 423, 424, are arranged along a longitudinal axis 435 of the medical device 414. In such embodiments, the hot regions 432, 433 of two adjacent Peltier elements 423, 424, face each other, or the cold regions 429, 430 of two adjacent Peltier elements 423, 424, face each other. In other words, the cold region 429 of one Peltier element 423 does not face the hot region 433 of an adjacent Peltier element 424. In some embodiments, the hydrophilic layer 438, covers the cold regions, e.g. 429 and 430. In some embodiments, the hydrophilic layer 438, covers the hot regions; for example, in such an embodiment, the orientation of both of the Peltier elements 423 and 424 along the axis 435 are flipped 180° so that hot regions 432 and 433 face each other.

In some embodiments, the means 426 of connecting Peltier elements 423, 424 to each other and to a power source 189 comprises a conductive polymer. In some embodiments, each Peltier element 423, 424 comprises alternating n-type semiconductor segments 444 and p-type semiconductor segments 447 arrayed around a perimeter 450 of the medical device 414, as shown in FIG. 8. In some embodiments, the medical device 414 further comprises a material 15 that possesses a Curie point below body temperature. In some embodiments the medical device 414 comprises a material 15 that possesses a Curie point above body temperature. The material 15 that possesses a Curie point, if present, may be present in all possible positions, arrangements and configurations in the medical device 414, as described for medical device 3 in FIG. 1.

Figure 9A:
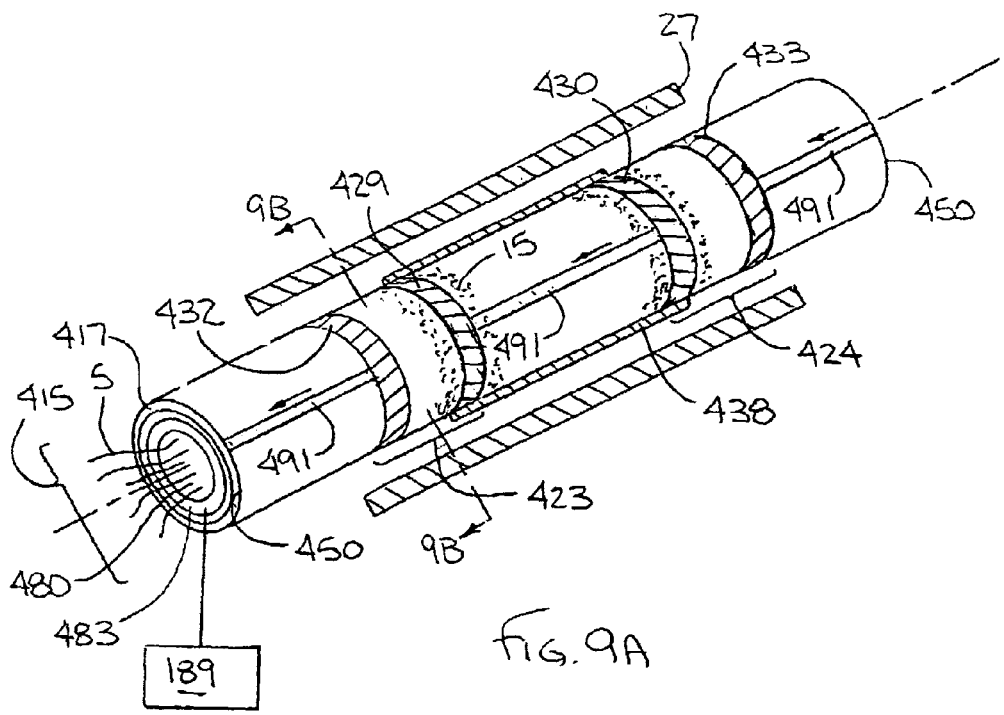
FIG. 9A is a perspective view of a medical device, constructed in accordance with the teachings of this disclosure, which comprises a housing surrounding a lumen, three layers, and at least one Peltier element arranged along a longitudinal axis of the medical device.
Figure 9B:
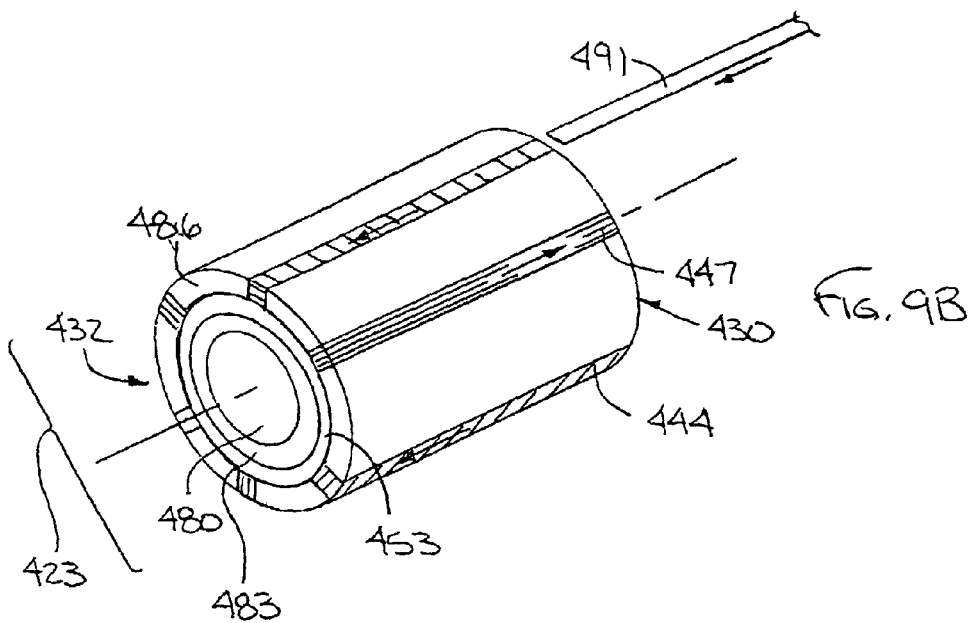
FIG. 9B is a partially sectioned perspective view of the medical device depicted in FIG. 9A taken along line 9B-9B of FIG. 9A.

FIG. 9A depicts a medical device 415, which is a variation of that shown in FIG. 8. Device 415 is adapted to be inserted into tissue and to be located using a magnetic resonance imaging device 27. The medical device 415 comprises a housing 417 surrounding a lumen 480. Three layers are depicted in FIG. 9B as contained within the housing 417 of the medical device 415. A first layer 483 surrounds the lumen 480. A second layer 453 surrounds the first layer 483. A third layer 486 surrounds the second layer 453. At least one passive Peltier element 423, 424 is arranged along a longitudinal axis 435 of the medical device 415. The first layer 483 comprises a conductive polymer. The second layer 453 comprises an isolating/insulating material. The third layer 486 comprises at least one Peltier element, e.g. 423, 424, and at least one stripe 491 of conducting polymer connecting the Peltier elements 423, 424 and to an external source of electricity 189. The stripe 491 and first layer 483, shown in FIGS. 9A and 9B, correspond to the means 426 shown in FIG. 8. The hot regions 432, 433, of two adjacent Peltier elements 423, 424 face each other, or the cold regions 429, 439 of two adjacent Peltier elements 423, 424 face each other. Each Peltier element 423, 424 comprises alternating n-type semiconductor segments 444 and p-type semiconductor segments 447 arrayed around the perimeter 450, and contained within the third layer 486 of the medical device 415 as shown in FIG. 9B. As the medical device in 415 is a variation of medical device 414, it may similarly include a hydrophilic layer 438 and a material 15 that possesses a Curie point.

Figure 10A:
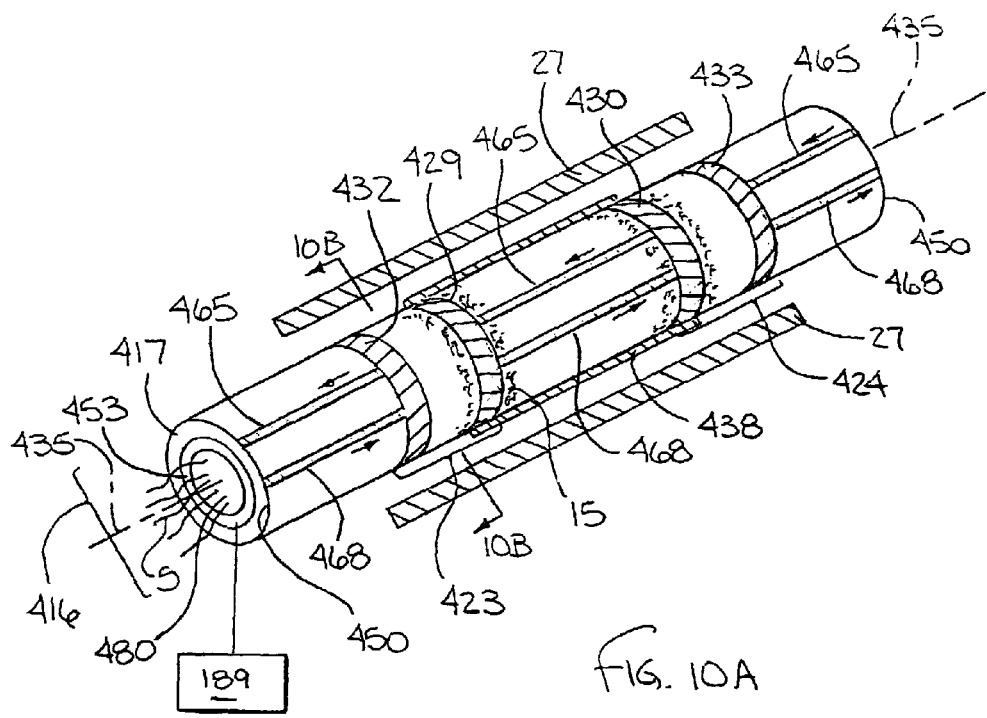
FIG. 10A is a perspective view of a variation of the medical device depicted in FIG. 9A, constructed in accordance with the teachings of this disclosure, wherein the first layer of the medical device depicted in FIG. 9A is absent, and wherein the third layer contains at least two stripes of conductive polymer.
Figure 10B:
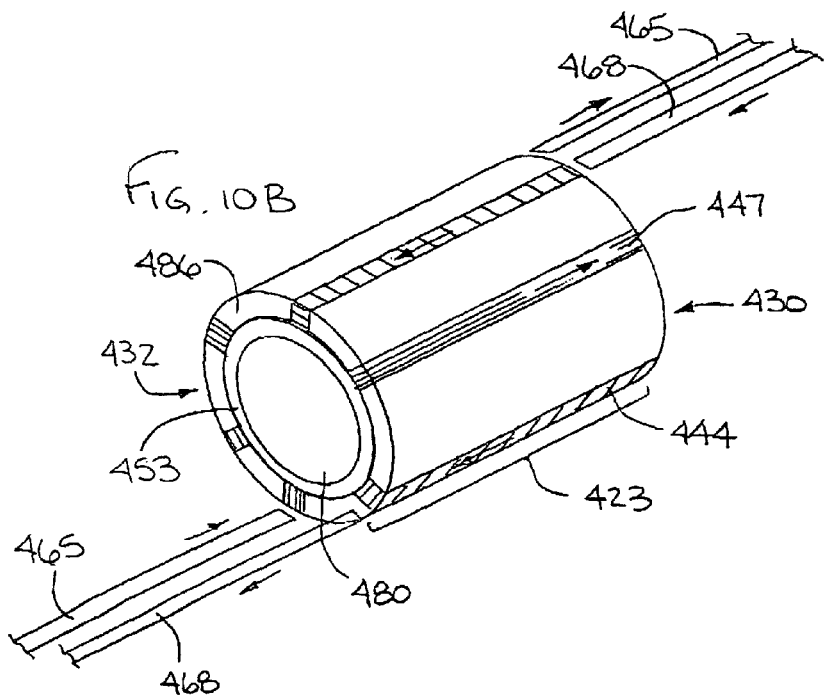
FIG. 10B is a partially sectioned view of the medical device depicted in FIG. 10A taken along line 10B-10B of FIG. 10A.

FIGS. 10A and 10B depict a medical device 416, which is another variation on that embodiment shown in FIGS. 9A and 9B. In the medical device 416 shown in FIGS. 10A and B, the first layer 483 is absent, and the third layer 486 contains at least two stripes: a first stripe 465 and a second stripe 468 of conductive polymer. The first stripe 465 and second stripe 468 serve as the means 426 shown in FIG. 8. Each Peltier element 423, 424 comprises at least three n-type semiconductor segments 444 and at least three p-type semiconductor segments 447. The first stripe 465 of conductive polymer is connected to n-type semiconductor segments 444 and p-type semiconductor segments 447 in each Peltier element 423, 424, wherein the number of n-type semiconductor segments 444 connected to the first stripe 465 is twice the number of p-type semiconductor segments 447 connected to the first stripe 465. The second stripe of conductive polymer 468 is connected to n-type semiconductor segments 444 and p-type semiconductor segments 447 in each Peltier element 423, 424, wherein the number of p-type semiconductor segments 447 connected to the second stripe 468 is twice the number of n-type semiconductor segments 444 connected to the second stripe 468. The first stripe 465 carries current in one direction along a longitudinal axis 435 of the medical device 414, and the second stripe 468 carries current in a direction opposite to the direction of the first stripe 465. As the medical device in 416 is a variation of medical device 414, it may similarly include a hydrophilic layer 438 and a material 15 that possesses a Curie point.

Figure 11:
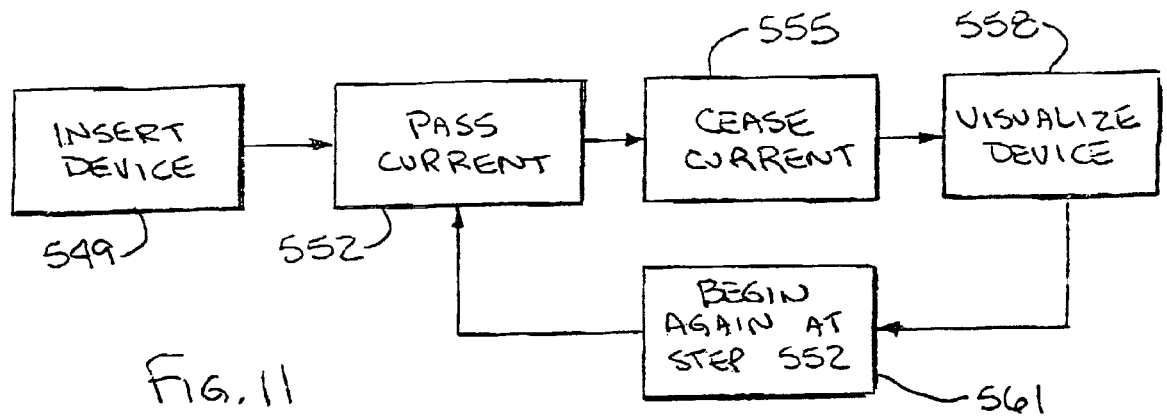
FIG. 11 is a flow chart depicting a method in accordance with the teachings of the disclosure.

FIG. 11 depicts a method for visualizing a medical device such as that depicted in FIG. 8. This method can be used in conjunction with medical devices 414, 415 and 416 shown in FIGS. 8, 9A, 9B, 10A and 10B, and other suitable medical devices as well. The method involves a medical device, e.g. 414, which comprises a housing 417, at least one Peltier element 423, each Peltier element being operatively associated with the housing 417, and a means 426 of connecting the Peltier elements 423 to each other and a power source 189. The method involves a first step 549 of inserting the medical device 414 into a subject. Next, in a step 552, electric current is passed through the medical device 414 in a direction so as to cool at least a portion of the medical device 414 relative to body temperature in order to see a sufficient effect (contrast) on a MRI. After that, in a step 555, the current traversing through the medical device 414 is ceased. Then, in a step 558, the medical device 414 is visualized using MRI.

Alternatively, the method depicted in FIG. 11 may further comprise an additional step 561, following the visualization step 558, of returning to the step 552 and repeating the cycle. In addition, the passing an electric current step 552 may further comprise cooling a hydrophilic layer 438 of the medical device 414. The method may further include cooling a material 15 operatively associated with the housing 417 that possesses a Curie point below body temperature so that the material becomes ferromagnetic.

The direction of the current applied in the passing the current step 552 can also be reversed so as to heat rather than cool at least a portion of the medical device 414 relative to body temperature in order to see a sufficient effect (contrast) on a magnetic resonance (MR) image. In such embodiments, the passing an electric current step 552 further may comprise heating the material 15 operatively associated with the medical device 414 that possesses a Curie point above body temperature so that the material 15 is no longer ferromagnetic.

Those medical device and method aspects and embodiments of the disclosure described above can utilize any kind of electro-active temperature modulator element, not just Peltier elements. Modifications can be made to the particular aspects and embodiments depending on the particular electro-active temperature modulator elements employed.

Figure 12:
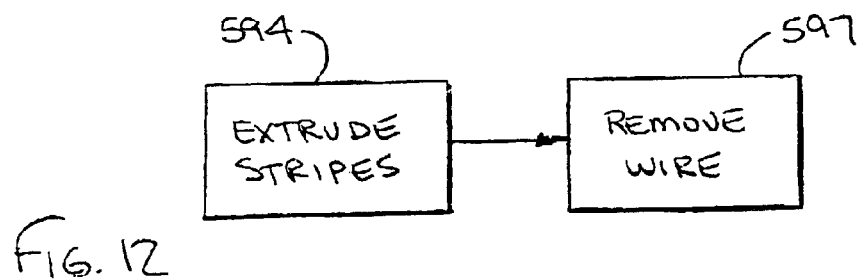
FIG. 12 is a flow chart depicting a method of manufacturing a medical device in accordance with the teachings of the disclosure.

FIG. 12 depicts a method of manufacturing a medical device, according to the present disclosure. The method may comprise the following steps. First, as indicated by reference number 594, two stripes of conducting polymer are extruded along a longitudinal axis of the medical device each of the stripes covering a metal wire that also runs along the longitudinal axis of the medical device. Next, as indicated by reference number 597, the wire is removed in those sections where a band (heating element) is desired to be located.

Figure 13:
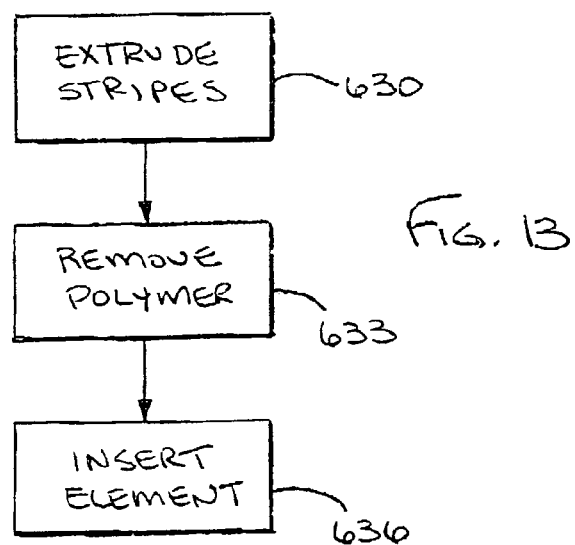
FIG. 13 is a flow chart depicting a method of manufacturing a medical device in accordance with the teachings of the disclosure.

FIG. 13 depicts an alternative method according to the disclosure for manufacturing a medical device, e.g. 416 shown in FIG. 10A. The method may comprise the following steps. First, as indicated by reference number 630, extruding at least two stripes of conducting polymer along a longitudinal axis of the medical device. Next, as indicated by reference number 633, the conductive polymer is removed in those sections where an electro-active temperature modulator element, such as a Peltier element, is to be inserted. After that, as indicated by reference number 636, electro-active temperature modulator elements are inserted in those areas where the conductive polymer has been removed.

All of the devices and methods taught by this exposure are capable of being used with human beings. Specifically, a medical device, e.g. 3, 147, 216, 414, 415, and 416, is capable of being inserted into tissue wherein that tissue is that of a human subject, and the methods herein described involve inserting a medical device into tissue wherein that tissue is that of a human subject. The tissue may be part of either a living or a deceased subject. While the devices and methods of this disclosure are can be used in human beings, they are also capable of being used in and with tissue of non-human subjects, including but not limited to mammals other than humans.

From the forgoing, one of ordinary skill in the art will appreciate that the disclosure teaches medical devices adapted to be inserted into tissue and to be located using a magnetic resonance imaging device, methods for visualizing such medical devices, as well as methods of manufacturing such medical devices. The devices and methods of this disclosure provide powerful new tools that will help advance the field of medicine.

What is claimed is:

1. A medical device adapted to be inserted into tissue and to be located using a magnetic resonance imaging device, comprising:
    a housing defining a lumen capable of accepting a fluid, the housing including a hydrophilic layer and a material having a Curie point, the hydrophilic layer and the material being outside the lumen; and
    a temperature modulator, the temperature modulator being operatively associated with the housing, the temperature modulator being configured to vary the temperature of the material past the Curie point, to alter the magnetic resonance image in response to a change in the temperature of the material.

2. The medical device of claim 1, wherein the medical device further comprises radiopaque material.

3. The medical device of claim 1, wherein the Curie point is in the range of 25 and 50 degrees Celsius.

4. The medical device of claim 1, wherein the Curie point is in the range of 32 and 42 degrees Celsius.

5. The medical device of claim 1, wherein the Curie point is within five degrees of body temperature.

6. The medical device of claim 1, wherein the material that possesses a Curie point comprises at least one element selected from the group consisting of cobalt, palladium, nickel, silicon, iron, manganese, chromium, and copper, so as to achieve a desired Curie point.

7. The medical device of claim 1, wherein the Curie point is above body temperature.

8. The medical device of claim 1, wherein the Curie point is below body temperature.

9. The medical device of claim 1, wherein the temperature modulator is capable of alternating the temperature of at least a portion of the medical device.

10. The medical device of claim 1, wherein the material having the Curie point is embedded within the hydrophilic layer.

11. A method, comprising:
inserting into tissue a medical device comprising a housing defining a lumen capable of accepting a fluid, a hydrophilic layer, a material having a Curie point, and a temperature modulator, the temperature modulator being operatively associated with the housing, the hydrophilic layer and the material being outside the lumen;
while the medical device is inserted into tissue, modulating a temperature of the medical device so that the temperature of the material is varied past the Curie point so as to modify the detectability of the medical device via magnetic resonance imaging; and
visualizing the medical device using magnetic resonance imaging.

12. The method of claim 11, wherein the material has a Curie point that is below body temperature.

13. The method of claim 11, wherein the material has a Curie point that is above body temperature.

14. The medical device of claim 11, wherein the material having the Curie point is embedded within the hydrophilic layer.

15. The method of claim 11, wherein the modulating step alters a temperature of the hydrophilic layer.

16. The method of claim 15, wherein the modulating step decreases the temperature of the hydrophilic layer.

17. The method of claim 15, wherein the modulating step decreases the temperature of the hydrophilic layer at least one degree Celsius.

18. The method of claim 15, wherein the modulating step increases the temperature of the hydrophilic layer.

19. The method of claim 15, wherein the modulating step increases the temperature of the hydrophilic layer at least one degree Celsius.

* * * * *